United States Patent [19]

Sugimori et al.

[11] Patent Number: 4,684,478
[45] Date of Patent: Aug. 4, 1987

[54] NOVEL LIQUID CRYSTAL COMPOUND FOR HIGH TEMPERATURES

[75] Inventors: Shigeru Sugimori, Fujisawashi; Yasuyuki Goto, Yokohamashi; Toyoshiro Isoyama, Yokohamashi; Kazunori Nigorikawa, Yokohamashi; Tetsuya Ogawa, Yokohamashi; Kisei Kitano, Yokohamashi; Naoyuki Yoshida, Kamakurashi; Yoshito Furukawa, Yokohamashi, all of Japan

[73] Assignee: Chisso Corporation, Tokyo, Japan

[21] Appl. No.: 816,740

[22] Filed: Jan. 6, 1986

[30] Foreign Application Priority Data

Jan. 7, 1985 [JP] Japan ..................... 60-715

[51] Int. Cl.$^4$ .................. C09K 19/30; C07C 13/00; C07C 15/12
[52] U.S. Cl. .................. 252/299.63; 252/299.5; 350/350 R; 350/350 S; 585/20; 585/25
[58] Field of Search ............ 252/299.5, 299.63; 250/350 S, 350 R; 585/20, 25

[56] References Cited

- U.S. PATENT DOCUMENTS

| | | | |
|---|---|---|---|
| 4,393,258 | 7/1983 | Sato et al. ................ | 252/299.63 |
| 4,419,263 | 12/1983 | Praefcke et al. .......... | 252/299.63 |
| 4,439,015 | 3/1984 | Rich et al. ............... | 252/299.63 |
| 4,472,592 | 9/1984 | Takatsu et al. ........... | 252/299.63 |
| 4,514,044 | 4/1985 | Gunjima et al. .......... | 252/299.63 |
| 4,526,704 | 7/1985 | Petrzilka et al. .......... | 252/299.63 |
| 4,583,326 | 4/1986 | Petrzilka et al. .......... | 252/299.63 |
| 4,606,845 | 8/1986 | Romer et al. ............. | 252/299.63 |
| 4,620,938 | 11/1986 | Romer et al. ............. | 252/299.63 |
| 4,637,897 | 1/1987 | Kelly ....................... | 252/299.63 |

FOREIGN PATENT DOCUMENTS

| | | | |
|---|---|---|---|
| 56501 | 7/1982 | European Pat. Off. ........ | 252/299.63 |
| 149208 | 7/1985 | European Pat. Off. ........ | 252/299.63 |
| 3211601 | 10/1983 | Fed. Rep. of Germany ................ | 252/299.63 |
| 3317597 | 11/1984 | Fed. Rep. of Germany ................ | 252/299.63 |
| 3410734 | 10/1985 | Fed. Rep. of Germany ................ | 252/299.63 |
| 3410733 | 10/1985 | Fed. Rep. of Germany ................ | 252/299.63 |
| 57-163324 | 10/1982 | Japan ..................... | 252/299.63 |
| 58-8023 | 1/1983 | Japan ..................... | 252/299.63 |
| 58-8022 | 1/1983 | Japan ..................... | 252/299.63 |
| 59-110630 | 6/1984 | Japan ..................... | 252/299.63 |
| 2092169 | 8/1982 | United Kingdom ........ | 252/299.63 |
| 2134110 | 8/1984 | United Kingdom ........ | 252/299.63 |

*Primary Examiner*—Teddy S. Gron
*Attorney, Agent, or Firm*—Wenderoth, Lind & Ponack

[57] ABSTRACT

A compound which, when added as a component to other components, raises the N-I point of the resulting liquid crystal composition and nevertheless affords only a relatively small rise in viscosity of the composition, and a liquid crystal composition containing the same are provided, which compound is a 1-(trans-4'-alkylcyclohexyl)-2-4''-[trans-4'''-(trans-4''''-alkylcyclohexyl)-cyclohexylphenyl]ethane expressed by the formula

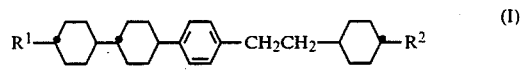

wherein $R^1$ and $R^2$ each represent an alkyl group of 1 to 10 carbon atoms.

4 Claims, No Drawings

NOVEL LIQUID CRYSTAL COMPOUND FOR HIGH TEMPERATURES

BACKGROUND OF THE INVENTION

This invention relates to a novel nematic liquid crystal compound of an ethane derivative useful as an electro-optical material, and a liquid crystal composition containing the same.

Display elements utilizing liquid crystals have been broadly used for watches, electric calculators, etc. These liquid crystal display elements utilize the optical anisotropy and dielectric anisotropy of liquid crystal substances, and the liquid crystal phases include nematic phase, smectic phase and cholesteric phase. However, among these display elements, those utilizing nematic liquid crystals have been most broadly practically used. They are classified into TN (twisted nematic) type, DS (dynamic scattering) type, guest-host type, DAP type, etc., and various characteristics are required for liquid crystal substances used for these respective display elements. Among the characteristics, however, an important one required for various display cells in common thereto is that a nematic phase is exhibited within a broad temperature range including room temperature. Most of practically usable materials having such a characteristic have usually been prepared by blending several kinds or more of components consisting of compounds having nematic phase in the vicinity of room temperature and compounds having nematic phase within a temperature region higher than room temperature. Most of liquid crystalline blends prepared as above and currently practically used have been required to have nematic phase over the whole temperature range of at least from $-30°$ C. to $+65°$ C. In order to satisfy such a requirement, the following compounds have often been used as the compounds having nematic phase within a temperature range higher than room temperature:

compounds having a crystalline phase-nematic phase transition point (C-N point) of about 100° C. and also having a nematic phase-isotropic liquid transition point (N-I point) of about 200° C., such as 4,4'-substituted-terphenyl, 4,4'-substituted-biphenylcyclohexane, 4,4'-substituted-benzoyloxybenzoic acid phenyl ester, etc.

These compounds, however, have undesirable properties of raising the viscosity of the resulting liquid crystalline blends to thereby retard the response rate.

SUMMARY OF THE INVENTION

The object of the present invention is to provide a novel liquid crystal compound having improved the above-mentioned properties and also a liquid crystal composition containing the same.

The present invention resides in a 1-(trans-4'-alkylcyclohexyl)-2-4''-[trans-4'''-(trans-4''''-alkylcyclohexyl)-cyclohexylphenyl]ethane expressed by the formula

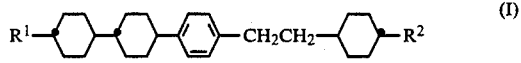
(I)

wherein $R^1$ and $R^2$ each represent an alkyl group of 1 to 10 carbon atoms, and a liquid crystal composition containing at least one kind of the same.

DESCRIPTION OF PREFERRED EMBODIMENTS

The compound of the formula (I) of the present invention has a good compatibility with other liquid crystal compounds such as those of biphenyls, esters, Schiff's bases, phenylcyclohexanes, heterocyclic compounds, etc.; a broad mesomorphic range; and a low viscosity. Thus, when the compound of the present invention is blended with other nematic liquid crystal compounds to thereby prepare a practically usable liquid crystalline blend having a broad mesomorphic range, it is possible to control the viscosity increase of the liquid crystalline blend to a less extent than that of the above known liquid crystal compounds.

$R^1$ and $R^2$ of the compound of the formula (I) each are preferred to be of linear chain, but compounds wherein $R^1$ and $R^2$ each are a branched chain alkyl group, also have a good compatibility and hence are useful as the case may be.

In addition, compounds of the following formulas similar to those of the formula (I) are known:

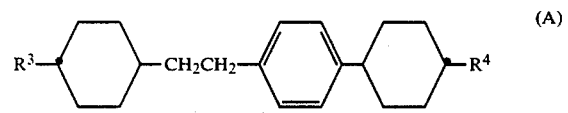
(A)

wherein $R^3$ and $R^4$ each represent an alkyl group of 1 to 5 carbon atoms (Japanese patent application laid-open No. Sho 57-163324/1982).

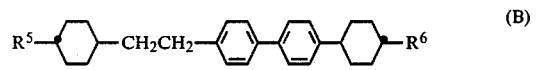
(B)

wherein $R^5$ and $R^6$ each represent an alkyl group of 1 to 7 carbon atoms (Japanese patent application laid-open No. Sho 58-8022/1983).

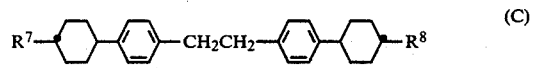
(C)

wherein $R^7$ and $R^8$ each represent an alkyl group of 1 to 7 carbon atoms (Japanese patent application laid-open No. Sho 58-8023/1983).

However, the compounds of the formula (A) raise a problem in the width of their mesomorphic ranges, while the compounds of the formulas (B) and (C) raise another problem in their compatibility with other liquid crystal compounds.

The compound of the formula (I) of the present invention may be prepared for example as follows:

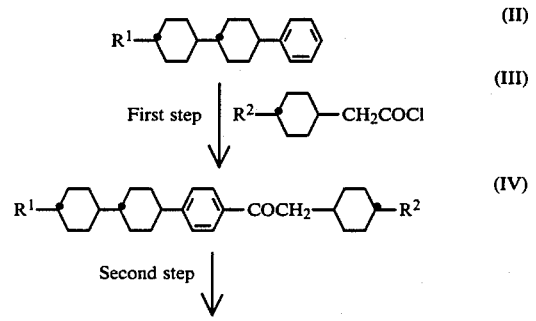

-continued

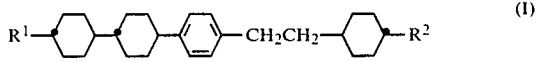

First, a compound of the formula (II) is reacted with a compound of the formula (III) and anhydrous $AlCl_3$ in $CS_2$ or nitrobenzene to prepare a compound of the formula (IV) (the first step).

The compound of the formula (IV) is then reacted with hydrazine and KOH in diethylene glycol or triethylene glycol to obtain the compound of the formula (I).

The present invention will be described in more detail by way of Examples.

EXAMPLE 1

Preparation of 1-(trans-4'-propylcyclohexyl)-2-4''-{trans-4'''-(trans-4''''-propylcyclohexyl)cyclohexylphenyl}ethane Anhydrous aluminum chloride (16.0 g, 0.120 mol) was added into $CS_2$ (100 ml), and trans-4-propylcyclohexylacetic acid chloride (20.3 g, 0.100 mol) was then dropwise added with stirring at room temperature, followed by cooling the mixture to 0° C., dropwise adding a solution of trans-4-(trans-4-propylcyclohexyl)-cyclohexylbenzene (28.4 g, 0.100 mol) dissolved in $CS_2$ (60 ml), with stirring for 2 hours, reacting the mixture at 0° C. for 5 hours, returning the temperature to room temperature, reacting the mixture for 2 hours, distilling off $CS_2$, adding the reaction mixture into ice water, agitating at 60° C. for one hour, cooling, extracting with ethyl ether (500 ml), washing the extraction fluid with water, drying, distilling off ethyl ether and recrystallizing from toluene to obtain a compound of the following formula (IV) (38.7 g, 0.086 mol):

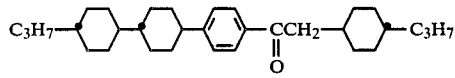

To this compound were added with stirring diethylene glycol (200 ml), hydrazine hydrate (21.5 g, 0.43 mol) and KOH (4.82 g, 0.258 mol), followed by raising the temperature gradually with stirring, reacting the mixture at 180° C. for 3 hours, allowing it to cool down to room temperature, adding water (500 ml), extracting the deposited crystals with toluene (200 ml), washing them with water, drying over anhydrous sodium sulfate, distilling off toluene and recrystallizing from benzene to obtain the captioned objective compound (23.3 g, 0.053 mol). This product exhibited liquid crystal phase and had a crystalline-smectic phase transition point (C-S point) of 57.7° C., a smectic phase-nematic phase transition point (S-N point) of 211.7° C. and a nematic phase-isotropic liquid phase transition point (N-I point) of 252.1° C.

EXAMPLE 2

1-(Trans-4'-propylcyclohexyl)-2-4''-[trans-4'''-(trans-4''''-ethylcyclohexyl)cyclohexylphenyl]ethane was prepared in the same manner as in Example 1. This compound had the following transition points: C-S point 45.9° C.; S-N point 204.1° C.; and N-I point 243.4° C.

EXAMPLE 3 (COMPOSITION EXAMPLE)

A liquid crystal composition (A) consisting of
trans-4-propyl-(4-cyanophenyl)cyclohexane 30% by weight,
trans-4-pentyl-(4-cyanophenyl)cyclohexane 40% by weight, and
trans-4-heptyl-(4-cyanophenyl)cyclohexane 30% by weight,
had a N-I point of 52° C. and a viscosity at 20° C. of 23.4 cp. To this liquid crystal composition (A) (85% by weight) was added 1-(trans-4'-propylcyclohexyl)-2-4''-[trans-4'''-(trans-4''''-propylcyclohexyl)cyclohexylphenyl]ethane (15% by weight) (a compound of the present invention obtained in Example 1). The N-I point of the resulting liquid crystal composition rose to 77° C., while its viscosity at 20° C. was 27 cp, that is, resulted in a relatively small increase.

Further, in order to evidence the effectiveness of the present invention, a comparative example was carried out wherein the following compound (15% by weight) which has been broadly used for raising the N-I point of liquid crystalline blends

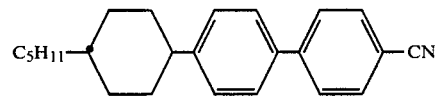

was added to the above liquid crystal composition (A) (85% by weight) to prepare a liquid crystal composition, which was subjected to measurement of phase transition point to give a N-I point of 72° C. and whose viscosity at 20° C. was 28 cp. From this fact, too, it will be understood that the compound of the present invention has a great effectiveness that its use raises the N-I point of the resulting liquid crystal composition and yet the accompanying rise in viscosity is inhibited.

EXAMPLE 4 (COMPOSITION EXAMPLE)

To the liquid crystal composition (A) (85% by weight) was added 1-(trans-4'-propylcyclohexyl)-2-4''-[trans-4'''-(trans-4''''-ethylcyclohexyl)cyclohexylphenyl]ethane (15% by weight) (a compound of the present invention obtained in Example 2). The N-I point of the resulting liquid crystal composition rose to 76.2° C., while its viscosity at 20° C. was 26.2 cp, that is, resulted in a relatively small increase.

What we claim is:
1. A 1-(trans-4'-alkylcyclohexyl)-2-4''-[trans-4'''-(trans-4''''-alkylcyclohexyl)cyclohexylphenyl]ethane expressed by the formula

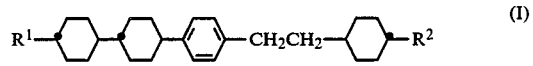

wherein $R^1$ and $R^2$ each represent an alkyl group of 1 to 10 carbon atoms.

2. A compound according to claim 1 wherein $R^1$ and $R^2$ in said formula (I) both represent $C_3H_7$.

3. A compound according to claim 1 wherein $R^1$ in said formula (I) represents $C_3H_7$ and $R^2$ therein represents $C_2H_5$.

4. A liquid crystal composition having at least two components at least one of which is a compound expressed by the formula (I) set forth in claim 1.

* * * * *